(12) United States Patent
Naya

(10) Patent No.: US 6,741,352 B2
(45) Date of Patent: May 25, 2004

(54) SENSOR UTILIZING ATTENUATED TOTAL REFLECTION

(75) Inventor: Masayuki Naya, Kaisei-machi (JP)

(73) Assignee: Fuji Photo Film Co., Ltd., Kanagawa-Ken (JP)

( * ) Notice: Subject to any disclaimer, the term of this patent is extended or adjusted under 35 U.S.C. 154(b) by 21 days.

(21) Appl. No.: 10/025,972

(22) Filed: Dec. 26, 2001

(65) Prior Publication Data

US 2002/0085203 A1 Jul. 4, 2002

(30) Foreign Application Priority Data

Dec. 25, 2000 (JP) ........................ 2000-392956

(51) Int. Cl.$^7$ .............................................. G01N 21/55
(52) U.S. Cl. ....................................................... 356/445
(58) Field of Search ................................ 356/445–448; 372/43, 45, 46

(56) References Cited

U.S. PATENT DOCUMENTS

| | | | |
|---|---|---|---|
| 4,821,276 A | * 4/1989 | Alphonse et al. | 372/45 |
| 4,821,277 A | * 4/1989 | Alphonse et al. | 372/45 |
| 4,844,613 A | 7/1989 | Batchelder et al. | |
| 5,370,114 A | 12/1994 | Wong et al. | |
| 5,804,453 A | 9/1998 | Chen | |
| 5,822,073 A | * 10/1998 | Yee et al. | 356/445 |
| 5,875,032 A | 2/1999 | Naya | |
| 6,577,396 B1 | * 6/2003 | Naya | 356/445 |
| 6,594,011 B1 | * 7/2003 | Kempen | 356/369 |

FOREIGN PATENT DOCUMENTS

| | | |
|---|---|---|
| EP | 0 863 395 A2 | 9/1998 |
| EP | 0 935 131 A2 | 11/1999 |
| JP | 6-167443 | 6/1994 |
| JP | 11326194 | 11/1999 |

OTHER PUBLICATIONS

Takayuki Okamoto, "Spectral Researches", Surface Refracto–Sensor Using Evanescent Waves Principles and Instrumentations, 1998, vol. 47; No. 1.

* cited by examiner

Primary Examiner—Michael P. Stafira
(74) Attorney, Agent, or Firm—Sughrue Mion, PLLC

(57) ABSTRACT

Disclosed herein is a sensor utilizing attenuated total reflection. The sensor is equipped with a prism, a metal film formed on a surface of the prism, an optical system for making a light beam enter the prism at various angles of incidence so that the condition for total internal reflection is obtained at the interface between the prism and the metal film, and photodetectors for detecting the light beam satisfying total internal reflection at the interface. In the sensor, a super luminescent diode is employed as a light source that emits the light beam.

3 Claims, 8 Drawing Sheets

F I G. 2
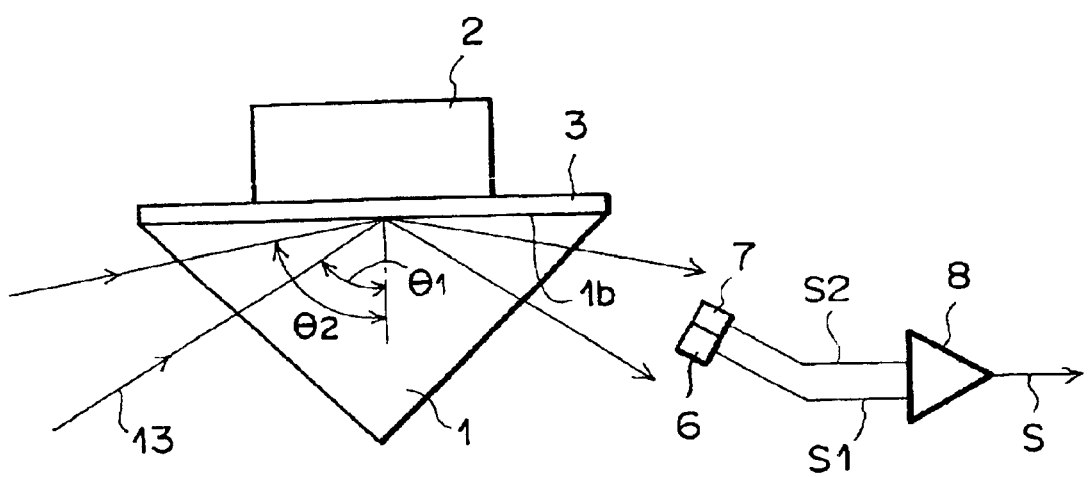

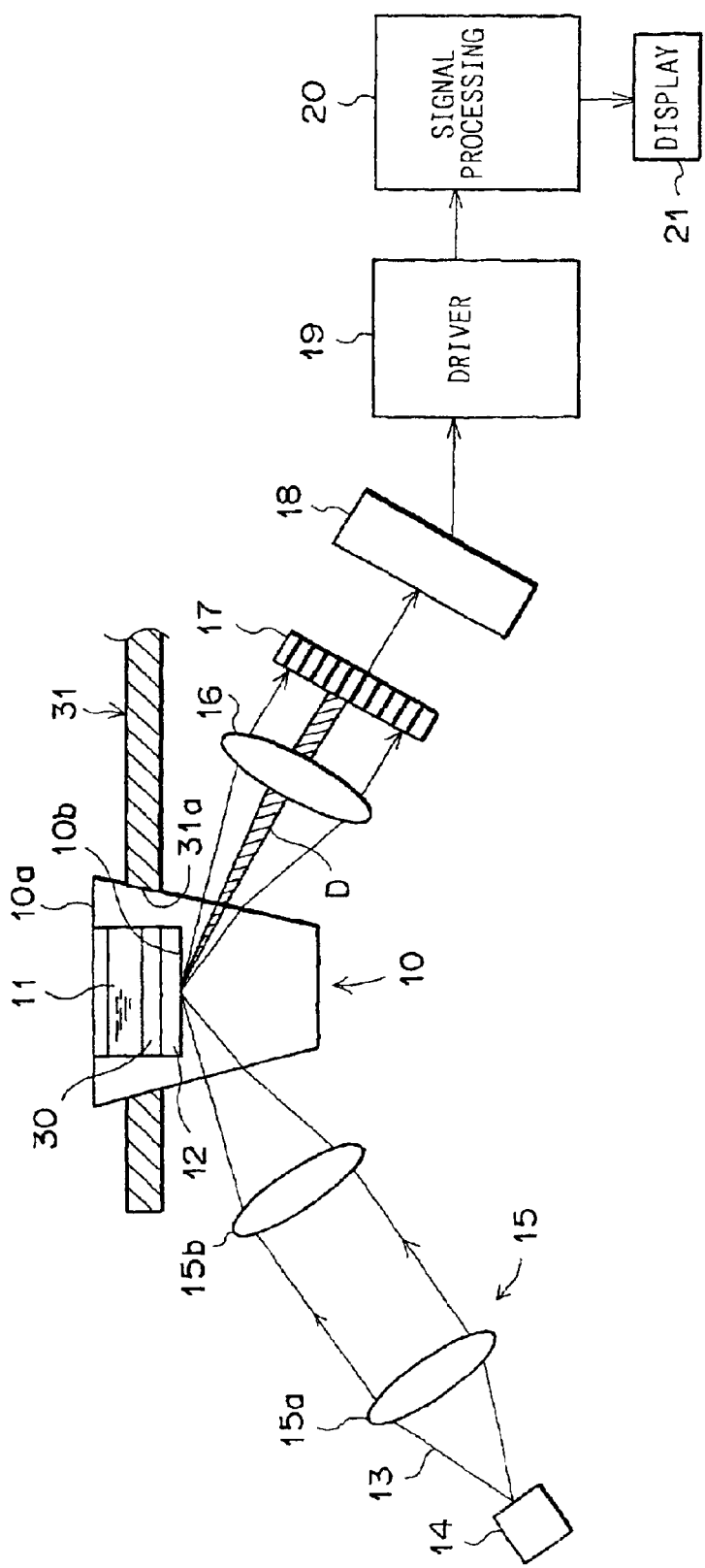

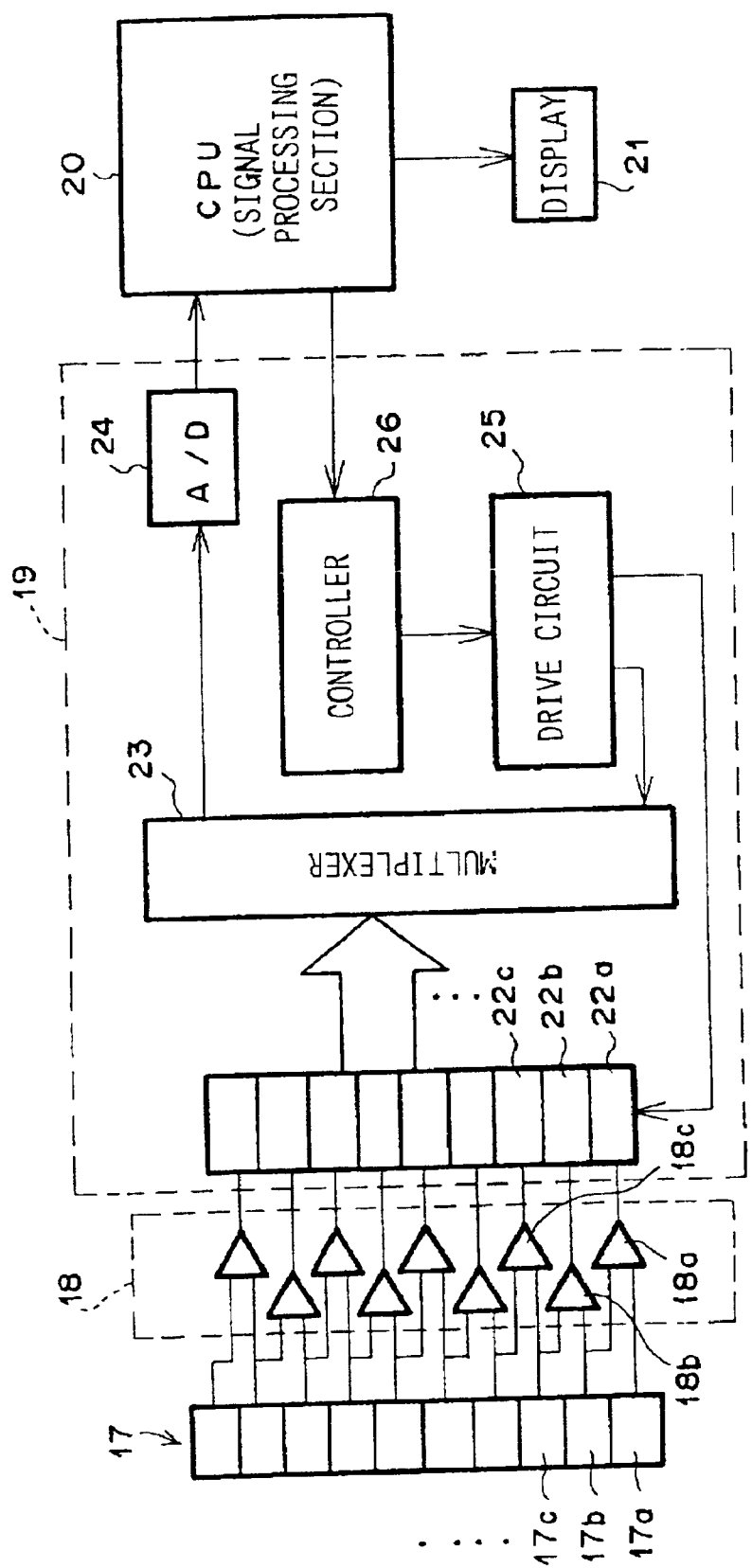

F I G. 6A
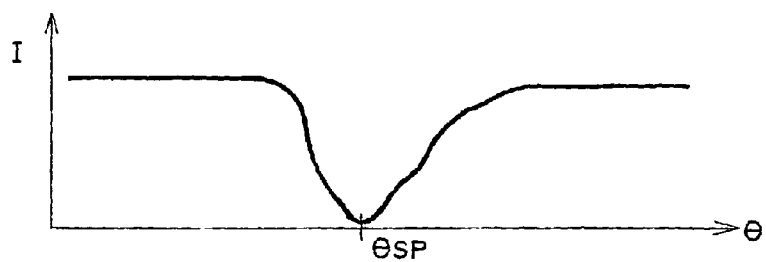
F I G. 6B
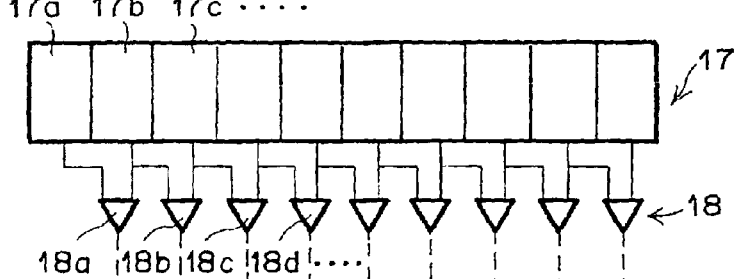
F I G. 6C
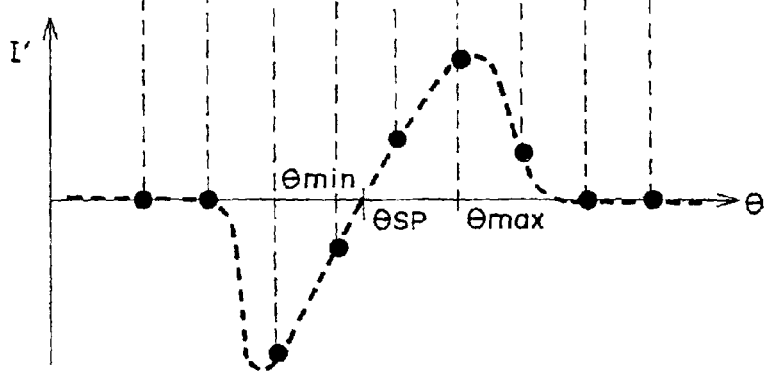

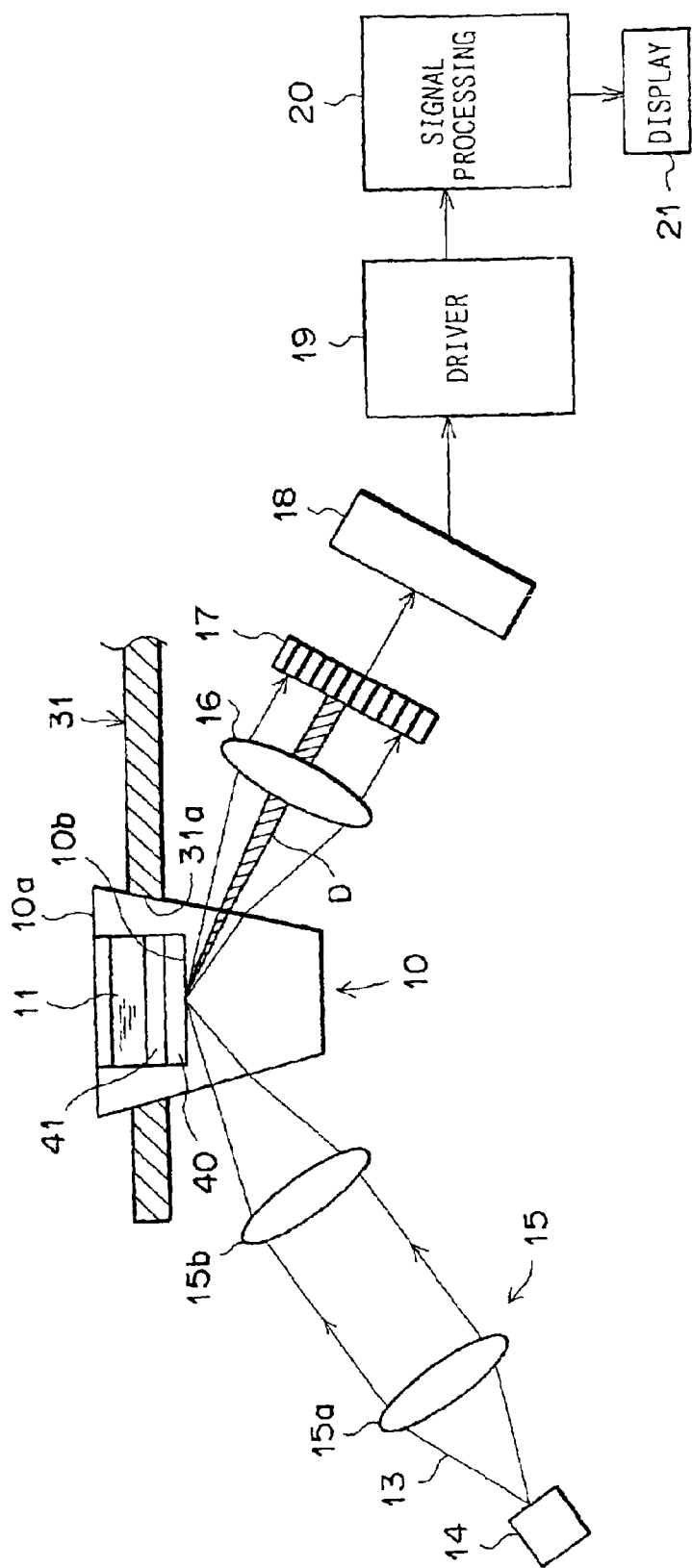

SENSOR UTILIZING ATTENUATED TOTAL REFLECTION

BACKGROUND OF THE INVENTION

1. Field of the Invention

The present invention relates to a sensor utilizing attenuated total reflection (hereinafter referred to as ATR), such as a surface plasmon resonance sensor for quantitatively analyzing a substance in a sample by utilizing the generation of surface plasmon, and more particularly to a sensor, utilizing ATR, which detects a dark line generated in a measuring light beam due to ATR by the use of photodetection means.

2. Description of the Related Art

In metals, if free electrons are caused to vibrate in a group, compression waves called plasma waves are generated. The compression waves generated in a metal surface are quantized into surface plasmon.

There have been proposed various surface plasmon resonance sensors for quantitatively analyzing a substance in a sample by taking advantage of a phenomenon that surface plasmon is excited by light waves. Among such sensors, one employing a system called "Kretschmann configuration" is particularly well known (e.g., see Japanese Unexamined Patent Publication No. 6(1994)-167443).

The surface plasmon resonance sensor employing the "Kretschmann configuration" is equipped mainly with a dielectric block formed, for example, into the shape of a prism; a metal film, formed on a surface of the dielectric block, for placing a sample thereon; a light source for emitting a light beam; an optical system for making the light beam enter the dielectric block at various angles of incidence so that the condition for total internal reflection is satisfied at the interface between the dielectric block and the metal film and that ATR can occur at the interface by surface plasmon resonance; and photodetection means for detecting the state of the surface plasmon resonance, that is, ATR, by measuring the intensity of the light beam satisfying total internal reflection at the interface.

In order to obtain various angles of incidence as described above, a relatively thin light beam may be caused to strike the above-mentioned interface at different angles of incidence, or relatively thick convergent or divergent rays may be caused to strike the interface so that they include components incident at various angles. In the former, the light beam whose reflection angle varies with a change in the incidence angle of the incident light beam can be detected by a small photodetector that is moved in synchronization with the incidence angle change, or by an area sensor extending in the direction in which the angle of reflection varies. In the latter, on the other hand, rays reflected at various angles can be detected by an area sensor extending in the direction in which all of the rays can be received.

In the surface plasmon resonance sensor mentioned above, if a light beam strikes the metal film at a specific incidence angle $\theta_{sp}$ equal to or greater than an angle at which total internal reflection occurs, evanescent waves having electric field distribution are generated in the sample in contact with the metal film, whereby surface plasmon is excited in the interface between the metal film and the sample. When the wave vector of the evanescent light is equal to the wave number of the surface plasmon and therefore the wave numbers between the two are matched, the evanescent waves and the surface plasmon resonate and light energy is transferred to the surface plasmon, whereby the intensity of light satisfying total internal reflection at the interface between the dielectric block and the metal film drops sharply. The sharp intensity drop is generally detected as a dark line by the above-mentioned photodetection means.

Note that the above-mentioned resonance occurs only when an incident light beam is p-polarized. Accordingly, a light beam must be p-polarized before it strikes the interface.

If the wave number of the surface plasmon is found from an incidence angle $\theta_{sp}$ at which ATR takes place, the dielectric constant of the sample can be obtained by the following Equation:

$$K_{sp}(\omega)=(\omega/c)\{\epsilon_m(\omega)\epsilon_s\}^{1/2}\{\epsilon_m(\omega)+\epsilon_s\}^{1/2}$$

where $K_{sp}$ represents the wave number of the surface plasmon, $\omega$ represents the angular frequency of the surface plasmon, c represents the speed of light in vacuum, and $\epsilon_m$ and $\epsilon_s$ represent the dielectric constants of the metal and the sample, respectively.

If the dielectric constant $\epsilon_s$ of the sample is known, then the density of the specific substance within the sample can be derived based on a predetermined calibration curve or the like. As a result, the incident angle $\theta_{sp}$ at which the aforementioned reflected light intensity drops can be known, thereby the properties relating to the dielectric constant, that is, the refractive index of the sample can be derived.

As a similar sensor making use of ATR, a leaky mode sensor is disclosed, for instance, in "Spectral Researches," Vol. 47, No. 1 (1998), pp. 21 to 23 and pp. 26 and 27. The leaky mode sensor is constructed mainly of a dielectric block in the form of a prism, for example; a cladding layer formed on a surface of the dielectric block; an optical waveguide layer, formed on the cladding layer, for placing a sample thereon; a light source for emitting a light beam; an optical system for making the light beam enter the dielectric block at various angles of incidence so that the condition for total internal reflection is satisfied at the interface between the dielectric block and the cladding layer and that ATR can occur at the interface by the excitation of an optical waveguide mode in the optical waveguide layer; and photodetection means for detecting the excited state of the waveguide mode, that is, ATR by measuring the intensity of the light beam satisfying total internal reflection at the interface.

In the leaky mode sensor with the construction mentioned above, if a light beam falls on the cladding layer through the dielectric block at angles of incidence equal to or greater than an angle at which total internal reflection occurs, the light beam is transmitted through the cladding layer and then only light with a specific wave number, incident at a specific angle, is propagated in the optical waveguide layer in a waveguide mode. If the waveguide mode is excited in this manner, the greater part of the incident light is confined within the optical waveguide layer, and consequently, ATR occurs in which the intensity of light satisfying total internal reflection at the above-mentioned interface drops sharply. Since the wave number of light propagating in the optical waveguide layer depends on the refractive index of the sample on the optical waveguide layer, the refractive index of the sample and/or the properties of the sample related to the refractive index can be analyzed by finding the above-mentioned specific incidence angle at which ATR occurs.

In the conventional surface plasmon resonance sensor and leaky mode sensor mentioned above, a laser is generally employed as the light source. Particularly, if a single mode laser is employed, the curve for ATR changes sharply and therefore a measurement can be made with high sensitivity. However, the emission wavelength of the laser is susceptible to influences from the outside and easily fluctuates. Because of this, there is a problem that it will become difficult to make a measurement with a high degree of accuracy. That is, if the emission wavelength of the laser fluctuates, it will have detrimental effects on the condition for generating surface plasmon (or the condition for exciting a waveguide mode) and cause noise to occur in a detection signal (which represents the intensity of light satisfying total internal reflection at the interface between the dielectric block and the thin film layer), resulting in a reduction in the accuracy of measurement.

Hence, to avoid the aforementioned problem, there has been proposed an apparatus employing a light-emitting diode (LED) as a light source. The LED has a great spectral line width and is not affected by wavelength fluctuation. However, since the spectral line width is too great, there is a problem that spectral sensitivity is low. In addition, the LED has the following disadvantages: since the light receiving area is large, angular resolution for ATR is low; and since light emitted from an LED is not linearly polarized light, a polarizing plate, etc., must be used and therefore the power of the measuring light is reduced.

SUMMARY OF THE INVENTION

The present invention has been made in view of the circumstances mentioned above. Accordingly, it is the primary object of the present invention to provide a sensor, utilizing ATR, which is capable of making a measurement with a high degree of accuracy.

To achieve this end and in accordance with an important aspect of the present invention, there is provided a sensor utilizing attenuated total reflection, comprising:

a dielectric block;

a thin film layer, formed on a surface of the dielectric block, for placing a sample thereon;

a light source for emitting a light beam;

an optical system for making the light beam enter the dielectric block at various angles of incidence so that the condition for total internal reflection is satisfied at an interface between the dielectric block and the thin film layer; and photodetection means for detecting the attenuated total reflection by measuring the intensity of the light beam satisfying total internal reflection at the interface;

wherein a semiconductor light emitting element that emits light by super radiance is employed as the light source.

In accordance with another important aspect of the present invention, structured particularly as a surface plasmon sensor, there is provided a sensor utilizing attenuated total reflection, comprising:

a dielectric block;

a metal film, formed on a surface of the dielectric block, for placing a sample thereon;

a light source for emitting a light beam;

an optical system for making the light beam enter the dielectric block at various angles of incidence so that the condition for total internal reflection is satisfied at an interface between the dielectric block and the metal film; and photodetection means for detecting the attenuated total reflection that results from surface plasmon resonance by measuring the intensity of the light beam satisfying total internal reflection at the interface;

wherein a semiconductor light emitting element that emits light by super radiance is employed as the light source.

In accordance with still another important aspect of the present invention, structured particularly as a leaky mode sensor, there is provided a sensor utilizing attenuated total reflection, comprising:

a dielectric block;

a cladding layer formed on a surface of the dielectric block;

an optical waveguide layer, formed on the cladding layer, for placing a sample thereon;

a light source for emitting a light beam;

an optical system for making the light beam enter the dielectric block at various angles of incidence so that the condition for total internal reflection is satisfied at an interface between the dielectric block and the cladding layer; and photodetection means for detecting the attenuated total reflection that results from excitation of a waveguide mode in the optical waveguide layer by measuring the intensity of the light beam satisfying total internal reflection at the interface;

wherein a semiconductor light emitting element that emits light by super radiance is employed as the light source.

The referent of the phrase "emits light by super radiance" is emission of light in which induced emission occurs but not emission of light by laser oscillation, due to the reflective structure of the element (refer to Japanese Unexamined Patent Publication Nos. 11(1999)-74559, and 9(1997)-232180, etc.).

A facet emission LED and a super luminescent diode (SLD) are examples of a semiconductor light emitting element that emits light by super radiance. The basic device structure of an SLD is similar to that of a semiconductor laser. However, the reflectance ratio of the facet thereof is low, in the order of less than 1%, and selectivity of the single mode is low, so light having a broad spectral width is emitted. Accordingly, it is a device that emits light having a broad spectral width like that of an LED, from a small facet like that of a semiconductor laser. For example, a super luminescent diode (AS2C211) manufactured by the Anritz Corporation is a point light source having a light emitting facet of 4 $\mu$m×1 $\mu$m, but its spectral line width is 17 nm.

Notice that the above-mentioned sensors utilizing ATR are capable of employing an area sensor, a line sensor, etc., as the photodetection means. More specifically, the sensors can suitably employ a two-piece photodiode, a photodiode array, etc.

In the sensors of the present invention utilizing ATR, a semiconductor light emitting element that emits light by super radiance is employed as a light source that emits a light beam. The SLD is a point light source similar to a semiconductor laser. Because of this, high angular resolution is obtained in the measurement of ATR, and a fluctuation in the emission wavelength (mode hop), which is causative of a reduction in the accuracy of measurement when a semiconductor laser is employed, does not occur. Thus, the present invention is capable of preventing noise that occurs in a measurement signal because of a fluctuation in the emission wavelength. As a result, a sample can be analyzed with a high degree of accuracy. In addition, the spectral line width is narrow compared with light-emitting diodes (LEDs), and high sensitivity is obtained compared with an apparatus employing an LED as a light source. Since the light beam is linearly polarized, the present invention is capable of eliminating the use of a polarizing plate, etc., required of LEDs. As a result, there is no power loss and sensitivity can be enhanced. Furthermore, in the case where a semiconductor layer is employed as a light source, the light beam is coherent and therefore there are cases where a reduction in the signal-to-noise ratio (S/N ratio) due to coherent noise becomes a problem. However, in the present invention, the light beam emitted from the SLD is incoherent, so that interference noise is less liable to occur. Thus, the S/N ratio can be enhanced.

That is, in the sensors of the present invention utilizing ATR, the semiconductor light emitting element that emits light by super radiance is employed as a light source, whereby sufficiently high accuracy of measurement is realized compared with the case where an LED or semiconductor laser is employed as a light source.

BRIEF DESCRIPTION OF THE DRAWINGS

The present invention will be described in further detail with reference to the accompanying drawings wherein:

FIG. 2 is a side view showing the surface plasmon detection section of the surface plasmon resonance sensor shown in FIG. 1;

FIG. 4 is a side view showing a surface plasmon resonance sensor in accordance with a second embodiment of the present invention;

FIG. 5 is a block diagram showing the electrical construction of the surface plasmon resonance sensor of the second embodiment shown in FIG. 4;

FIG. 6A is a graph showing the relationship between the incidence angle of a light beam and the intensity of the light beam, obtained according to the surface plasmon resonance sensor of the second embodiment shown in FIG. 4;

FIG. 6B is a diagram showing a photodiode array employed in the surface plasmon resonance sensor of the second embodiment shown in FIG. 5;

FIG. 6C is a graph showing the relationship between the incidence angle of the light beam and the differentiated value of the output of the photodiode array; and FIG. 7 is a side view showing a leaky mode sensor in accordance with a third embodiment of the present invention.

DESCRIPTION OF THE PREFERRED EMBODIMENTS

Referring now in greater detail to the drawings and initially to FIG. 1, a sensor of a first embodiment of the present invention utilizing attenuated total reflection (hereinafter referred to as ATR), which is a surface plasmon resonance sensor utilizing surface plasmon resonance, will be described.

Figure 1:
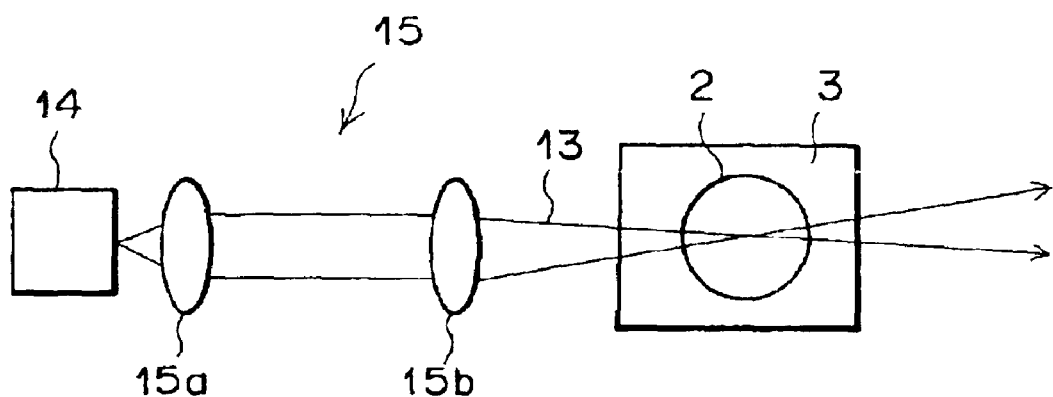
FIG. 1 is a plan view showing the optical system and sensor section of a surface plasmon resonance sensor in accordance with a first embodiment of the present invention.

As shown in FIG. 1, the surface plasmon resonance sensor is equipped with a triangular glass prism 1 (which is one form of a dielectric block) formed from glass that is a dielectric. The major axis of the prism 1 extends in a direction perpendicular to the paper surface of FIG. 2 (or a vertical direction in FIG. 1). The surface plasmon resonance sensor is also equipped with a metal film 3 formed on a surface of the prism 1. The metal film 3 is composed, for example, of gold, silver, etc. A sample 2 to be analyzed is placed on the metal film 3. The surface plasmon resonance sensor is further equipped with a light source 14, which consists of a super luminescent diode (hereinafter referred to as a SLD 14), for emitting a single light beam 13; an optical system 15 for making the light beam 13 enter the prism 1 so that various angles of incidence are obtained with respect to the interface 1b between the prism 1 and the metal film 3; a first photodetection means 6 and a second photodetection means 7 for detecting the light quantity of the light beam 13 satisfying total internal reflection at the interface 1b; and a comparator 8, connected to these photodetection means 6 and 7.

The optical system 15 consists of a collimator lens 15a for collimating the light beam 13 emitted divergently from the SLD 14, and a condenser lens 15b for making the collimated light beam 14 converge on the interface 1b.

Since it is focused as described above by the condenser lens 15b, the lightbeam13 includes components incident at various incidence angles θ with respect to the interface 1b. As illustrated in FIG. 2, the incidence angle θ varies between the minimum incidence angle $\theta_1$ and the maximum incidence angle $\theta_2$, and is greater than or equal to an angle at which total internal reflection occurs. Hence, the light beam 13 is reflected at the interface 1b so that it satisfies total internal reflection. The reflected light beam 13 includes components reflected at various angles. Note that the optical system 15 may be constructed so that the light beam 13 in a defocused state impinges on the interface 1b. If done in this manner, errors in detecting the state of the surface plasmon resonance (e.g., errors in measuring the position of the aforementioned dark line) are averaged, whereby the accuracy of measurement is enhanced.

Note that the light beam 13 is p-polarized and impinges on the interface 1b. For this reason, the SLD 14 needs to be disposed so that the polarization direction thereof becomes a predetermined direction. Alternatively, the polarization direction of the light beam 13 maybe controlled with a wavelength plate, etc.

On the other hand, the first photodetection means 6 and the second photodetection means 7 consist of a two-piece photodiode by way of example. The first photodetection means 6 is disposed to detect the light quantity of the components, which are within a first range of relatively low reflection angles, of the light beam 13 satisfying total internal reflection at the interface 1b. The second photodetection means 7 is disposed to detect the light quantity of the components, which are within a second range of relatively high reflection angles, of the light beam 13 satisfying total internal reflection at the interface 1b.

As described above, the first embodiment employs the SLD 14 as a light source that emits the light beam 13. The SLD 14 is a point light source similar to a semiconductor laser. Because of this, high angular resolution is obtained in the measurement of ATR, and a fluctuation in the emission wavelength (mode hop), which is causative of a reduction in the accuracy of measurement when a semiconductor laser is employed, does not occur. Thus, the first embodiment is capable of preventing noise that occurs in a measurement signal because of a fluctuation in the emission wavelength. In addition, the spectral line width is narrow compared with light-emitting diodes (LEDs), and high sensitivity is obtained compared with an apparatus employing an LED as a light source. Since the light beam 13 is linearly polarized, the use of a polarizing plate, etc., required of LEDs, is eliminated. As a result, there is no power loss and sensitivity can be enhanced. In the case where a semiconductor layer is employed as a light source, the light beam is coherent and therefore there are cases where a reduction in the signal-to-noise ratio (S/N ratio) due to coherent noise becomes a problem. However, the light beam emitted from the SLD 14 of the first embodiment is incoherent, so that interference noise is less liable to occur. Thus, the S/N ratio can be enhanced.

A description will hereinafter be given of how the sample 2 is analyzed by the surface plasmon resonance sensor constructed as described above. The sample 2 is first held in contact with the metal film 3. Then, the light beam 13, focused as described above, is irradiated toward the metal film 3. The light beam 13 satisfying total internal reflection at the interface 1b is detected by the first photodetection means 6 and the second photodetection means 7.

The first photodetection means 6 and the second photodetection means 7 output a first light-quantity detection signal S1 and a second light-quantity detection signal S2 to the comparator 8, respectively. The comparator 8 outputs a differential signal S representing the difference between the two signals S1 and S2.

Figure 3A:
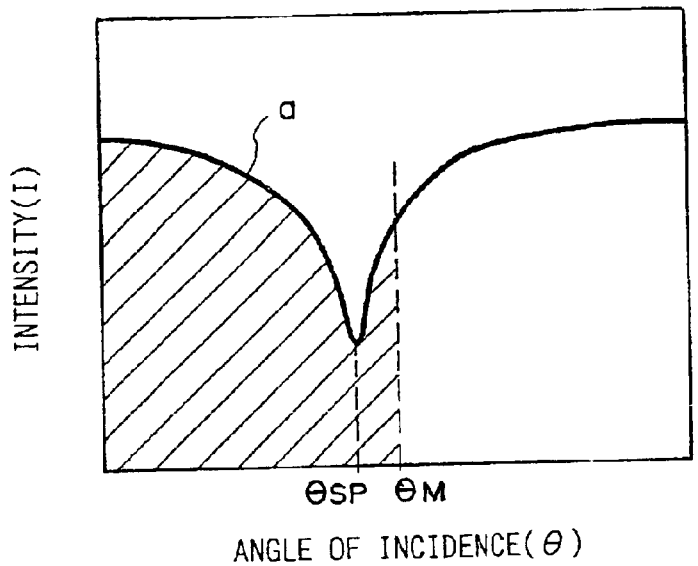
FIGS. 3A and 3B are graphs showing the relationship between the incidence angle of a light beam and the light intensity detected by the photodetection means, obtained according to the surface plasmon resonance sensor of the first embodiment.
Figure 3B:
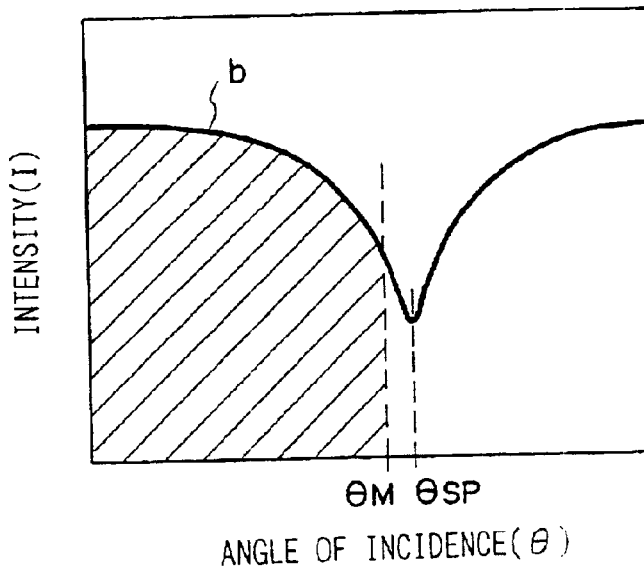

Note that the light, incident at a specific incidence angle $\theta_{sp}$ on the interface 1b, excites surface plasmon at the interface 1b between the metal film 3 and the sample 2. Because of this, the intensity I for the reflected light drops sharply. The relationship between the intensity I for the light beam 13 satisfying total internal reflection at the interface and the incidence angle $\theta$ is shown by curves a and b in FIGS. 3A and 3B. If the incidence angle $\theta_{sp}$ for ATR and the relational curve between the reflected-light intensity I and the incidence angle $\theta$ are found, a specific substance in the sample 2 can be quantitatively analyzed. The reason for this will hereinafter be described in detail.

For example, if the first reflection angle range and the second reflection angle range are continuous to each other, and the angle of reflection at the boundary between the two ranges is taken to be $\theta_M$, the light in a range where the incidence angle is less than the incidence angle $\theta_M$ is detected by one of the two photodetection means 6 and 7, and the light in a range where the incidence angle is greater than the incidence angle $\theta_M$ is detected by the other of the two photodetection means 6 and 7.

As an example, assume that the light in a range where the incidence angle is less than the incidence angle $\theta_M$ is detected by the first photodetection means 6, and that the light in a range where the incidence angle is greater than the incidence angle $\theta_M$ is detected by the second photodetection means 7. In this case, the first photodetection means 6 detects light in the ranges shaded in FIGS. 3A and 3B, and the detected light quantity in the case of FIG. 3B becomes greater than that in the case of FIG. 3A. Conversely, for the light quantity detected by the second photodetection means 7, the case of FIG. 3B becomes smaller than the case of FIG. 3A. Thus, between the light quantity detected by the first photodetection means 6 and the light quantity detected by the second photodetection means 7, there is a particular difference corresponding to the relationship between the incidence angle $\theta$ and the reflected-light quantity I.

Therefore, if reference is made to an analytical curve for each sample previously obtained, the incidence angle $\theta_{sp}$ for ATR and the relational curve between the incidence angle $\theta$ and the reflected-light quantity I, relating to the sample 2, can be estimated based on the output of the comparator 8 indicating the difference between the first light quantity detection signal S1 output from the first photodetection means 6 and the second light quantity detection signal S2 output from the second photodetection means 7, that is, the differential signal S. Thus, a substance in the sample 2 can be quantitatively analyzed.

The first embodiment has been described with reference to the case where the first reflection angle range and the second reflection angle range are continuous to each other. However, even when the two ranges are not continuous, a substance in the sample 2 can be quantitatively analyzed in the same manner, because a particular difference, corresponding to the incidence angle $\theta$ and the reflected-light quantity I, develops between the light quantity detected by the first photodetection means 6 and the light quantity detected by the second photodetection means 7.

FIG. 4 shows a sensor constructed according to a second embodiment of the present invention. Note in the figure that the same reference numerals are applied to the same parts as those in FIG. 1 and that a description thereof will not be given unless particularly necessary.

The sensor of the second embodiment utilizing ATR, as with the first embodiment, is a surface plasmon resonance sensor utilizing surface plasmon resonance. The surface plasmon resonance sensor includes a dielectric body 10 formed, for example, into the shape of a generally quadrangular pyramid, and a metal film 12, formed on a surface (top surface in FIG. 4) of the dielectric body 10, which consists, for example, of gold, silver, copper, aluminum, etc.

The dielectric block 10 is formed, for example, from transparent resin or the like, and is thickened at a portion 10a thereof to form a sample holder portion in which a liquid sample 11 is stored. In the second embodiment, a sensing medium 30 (which is to be described later) is placed on the metal film 12.

The dielectric block 10, along with the metal film 12, constitutes a disposable measuring chip. The measuring chip is fitted in each of the chip holding holes 31a formed in a turntable 31. With the dielectric blocks 10 thus fitted in the chip holding holes 31a of the turntable 31, the turntable 31 is intermittently rotated by a predetermined angle at a time. If a dielectric block 10 is stopped at a predetermined position, the liquid sample 11 is dropped into the dielectric block 10 and held within the sample holding portion 10a. If the turntable 31 is further rotated by a predetermined angle, the dielectric block 10 is moved to the measuring position shown in FIG. 1 and stopped there.

The surface plasmon resonance sensor of the second embodiment, in addition to the dielectric block 10, is equipped with a light source 14, which consists of a super luminescent diode (hereinafter referred to as a SLD 14), for emitting a light beam 13; an optical system 15 for making the light beam 13 enter the dielectric block 10 so that various angles of incidence are obtained with respect to the interface 10b between the dielectric block 10 and the metal film 12; and a collimator lens 16 for collimating the light beam 13 satisfying total internal reflection at the interface 10b. The surface plasmon resonance sensor of the second embodiment is further equipped with photodetection means 17 for detecting the collimated light beam 13; a diffusing plate 27, disposed between the collimator lens 16 and the photodetection means 17, for diffusing the light beam 13; a differential amplifier array 18 connected to the photodetection means 17; a driver 19, a signal processing section 20 constructed of a computer system, etc.; and display means 21 connected to the signal processing section 20.

As shown in FIG. 4, the light beam 13 emitted divergently from the SLD 14 is converged on the interface 10b between the dielectric block 10 and the metal film 12 by the optical system 15. Therefore, the light beam 13 includes components incident at various incidence angles θ with respect to the interface 10b. Note that the incidence angles θ are equal to or greater than an angle at which total internal reflection occurs. Hence, the light beam 13 is reflected at the interface 10b so that it satisfies total internal reflection. The reflected light beam 13 includes components reflected at various angles.

The light beam satisfying total internal reflection at the interface 10b is collimated by the collimator lens 16 and is detected by the photodetection means 17. The photodetection means 17 in the second embodiment is a photodiode array consisting of a plurality of photodiodes 17a, 17b, 17c, ... arranged in a row. As shown in FIG. 4, the direction in which the photodiodes are arranged is approximately perpendicular to the traveling direction of the collimated light beam 13. Therefore, each of the components of the light beam 13 satisfying total internal reflection at the interface 10b at various angles are separately received by different photodiodes 17a, 17b, 17c, ....

FIG. 5 shows the electrical construction of the surface plasmon resonance sensor of the second embodiment. As shown in the figure, the driver 19 is constructed of sample holding circuits 22a, 22b, 22c, ... for holding the outputs of the differential amplifiers 18a, 18b, 18c, ... of the differential amplifier array 18; a multiplexer 23 to which the outputs of the sample holding circuits 22a, 22b, 22c, ... are input; an A/D converter 24 for digitizing the output of the multiplexer 23 and then inputting the digitized output to the signal processing section 20; a drive circuit 25 for driving the multiplexer 23 and the sample holding circuits 22a, 22b, 22c, ...; and a controller 26 for controls operation of the drive circuit 25 in response to a control signal from the signal processing section 20.

The outputs of the photodiodes 17a, 17b, 17c, ... are input to the differential amplifiers 18a, 18b, 18c, ... of the differential amplifier array 18. Note that the outputs of two adjacent photodiodes are input in common to a single differential amplifier. Therefore, the outputs of the differential amplifiers 18a, 18b, 18c, ... are considered to be values obtained by differentiating the photodetection signals output from the photodiodes 17a, 17b, 17c, ... in the direction where the photodiodes are arranged.

The outputs of the differential amplifiers 18a, 18b, 18c, ... are held at predetermined timings by the sample holding circuits 22a, 22b, 22c ..., respectively, and are input to the multiplexer 23. The multiplexer 23 inputs the held outputs of the differential amplifiers 18a, 18b, 18c, ... to the A/D converter 24 in a predetermined order. The A/D converter 24 digitizes these outputs and then inputs the digitized signals to the signal processing section 20.

FIG. 6A shows the relationship between the incidence angle θ of the light beam 13 with respect to the interface 10b and the above-mentioned light intensity I. Light, incident at a specific angle $\theta_{sp}$ on the interface 10b between the metal film 12 and the sample 11, generates surface plasmon on the interface 10b. For this reason, the intensity I of the reflected light drops sharply. That is, the specific incidence angle $\theta_{sp}$ is an angle at which light does not meet the condition for total internal reflection. At the incidence angle $\theta_{sp}$, the reflected-light intensity I becomes the minimum value. The sharp drop in the reflected-light intensity I is observed as a dark line in the reflected light, as shown at D in FIG. 4.

FIG. 6B shows the direction in which the photodiodes 17a, 17b, 17c, ... are arranged in a row. As described previously, the positions of the photodiodes 17a, 17b, 17c, ... correspond univocally to the above-mentioned incidence angles θ.

FIG. 6C shows the relationship between the positions of thephotodiodes 17a, 17b, 17c, ... (i.e., the incidence angles θ) and the outputs I' of the differential amplifiers 18a, 18b, 18c, ... (i.e., differentiated values of reflected-light intensities I).

Based on the differentiated value I' input from the A/D converter 24, the signal processing section 20 selects a differential amplifier (e.g., the differential amplifier 18d in FIG. 6) whose output is closest to a differentiated value I'=0 corresponding to the aforementioned incident angle $\theta_{sp}$, from among the differential amplifiers 18a, 18b, 18c, .... Then, a predetermined correction process is performed on a differentiated value I' output from the selected differential amplifier. The corrected value is displayed on the display means 21. Note that there are cases where a differential amplifier outputting a differentiated value I'=0 is present. In that case, it is a matter of course that that differential amplifier is selected.

Thereafter, each time a predetermined time elapses, the differentiated value I' output from the selected differential amplifier 18d is subjected to a predetermined correction process, and is displayed on the display means 21. If the dielectric constant or refractive index of the substance in contact with the metal film 12 (see FIG. 4) in the measuring chip changes and therefore the curve in FIG. 6A is shifted in a horizontal direction, the differentiated value I' is increased or decreased according to the shift. Therefore, by continuously measuring the differentiated value I' with the lapse of time, a change in the refractive index of the substance in contact with the metal film 12, that is, a change in the property of the substance, can be detected.

Particularly, in the second embodiment, the sensing medium 30 that couples with a specific substance in the liquid sample 11 is placed on the metal film 12, and according to the coupled state, the refractive index of the sensing medium 30 changes. Therefore, by continuously measuring the differentiated value I', how the coupled state changes can be detected. In this case, both the liquid sample 11 and the sensing medium are samples that are to be analyzed. As a combination of the specific substance and the sensing medium 30, there is, for instance, a combination of antigen and antibody.

As described above, the second embodiment employs the photodiode array, consisting of a plurality of photodiodes 17a, 17b, 17c, ... arranged in a row, as the photodetection means 17. Therefore, even if the curve in FIG. 6A is greatly shifted in a horizontal direction according to a change in the liquid sample 11, the dark line can be detected. That is, the use of the photodetection means 17 in the form of an array makes it possible to assure a large dynamic range of measurements.

Note that the differential amplifier array 18, consisting of differential amplifiers 18a, 18b, 18c ..., may be replaced with a single differential amplifier. In this case, the outputs of the photodiodes 17a, 17b, 17c, ... are switched by a multiplexer so that two adjacent outputs are input in sequence to the single differential amplifier.

Notice that in order to observe how the coupled state between the specific substance in the liquid sample 11 and the sensing medium 30 changes with the lapse of time, the differentiated value I' may be calculated and displayed each time a predetermined time elapses and, in addition, the difference ΔI' between the initial differentiated value I' (0) and the differentiated value I' (t) measured when a predetermined time elapses, may be calculated and displayed.

FIG. 7 shows a sensor constructed according to a third embodiment of the present invention. Note in the figure that the same reference numerals are applied to the same parts as those in FIG. 1 or 4 and that a description thereof will not be given unless particularly necessary.

The sensor of the third embodiment utilizing ATR is a leaky mode sensor as previously described. As with the second embodiment, the third embodiment is constructed so that it employs a plurality of dielectric blocks 10 as measuring chips. Each dielectric block 10 has a cladding layer 40 on a surface thereof (e.g., the top surface in FIG. 7), and an optical waveguide layer 41 is formed on the cladding layer 40.

The dielectric block 10 is formed, for example, from synthetic resin, or optical glass such as BK7, etc. The cladding layer 40 is formed into the shape of a thin film from a dielectric lower in refractive index than the dielectric block 10, or metal such as gold, etc. The optical waveguide layer 41 is also formed into the shape of a thin film from a dielectric higher in refractive index than the cladding layer 40, such as polymethylmethacrylate (PMMA). The cladding layer 40 is 36.5 nm in thickness when it is formed from a thin gold film. The optical waveguide layer 41 is 700 nm in thickness when it is formed from PMMA.

In the leaky mode sensor of the third embodiment, if a light beam 13 emitted from a SLD 14 impinges on the cladding layer 40 through the dielectric block 10 at incidence angles equal to or greater than an angle at which total internal reflection occurs, the light beam 13 satisfies total internal reflection at an interface 10b between the dielectric block 10 and the cladding layer 40. However, light with a specific wave number, incident on the optical waveguide layer 41 through the cladding layer 40 at a specific incidence angle, propagates in the optical waveguide layer 41 in a waveguide mode. If the waveguide mode is thus excited, the greater part of the incident light is confined within the optical waveguide layer 41, and consequently, ATR occurs in which the intensity of light satisfying total internal reflection at the interface 10b drops sharply.

Since the wave number of light propagating in the optical waveguide layer 41 depends on the refractive index of the sample 11 on the optical waveguide layer 41, the refractive index of the sample 11 and/or the properties of the sample 11 related to the refractive index can be analyzed by finding the above-mentioned specific incidence angle at which ATR occurs. In addition, the properties of the sample 11 can be analyzed based on the reflected-light intensity I near the above-mentioned specific incidence angle, or the differentiated value I' output from each differential amplifier of a differential amplifier array 18.

The second and third embodiments are capable of analyzing a sample with a high degree of accuracy, because they employ the SLD 14 as the light source, as with the first embodiment.

Figure 8:
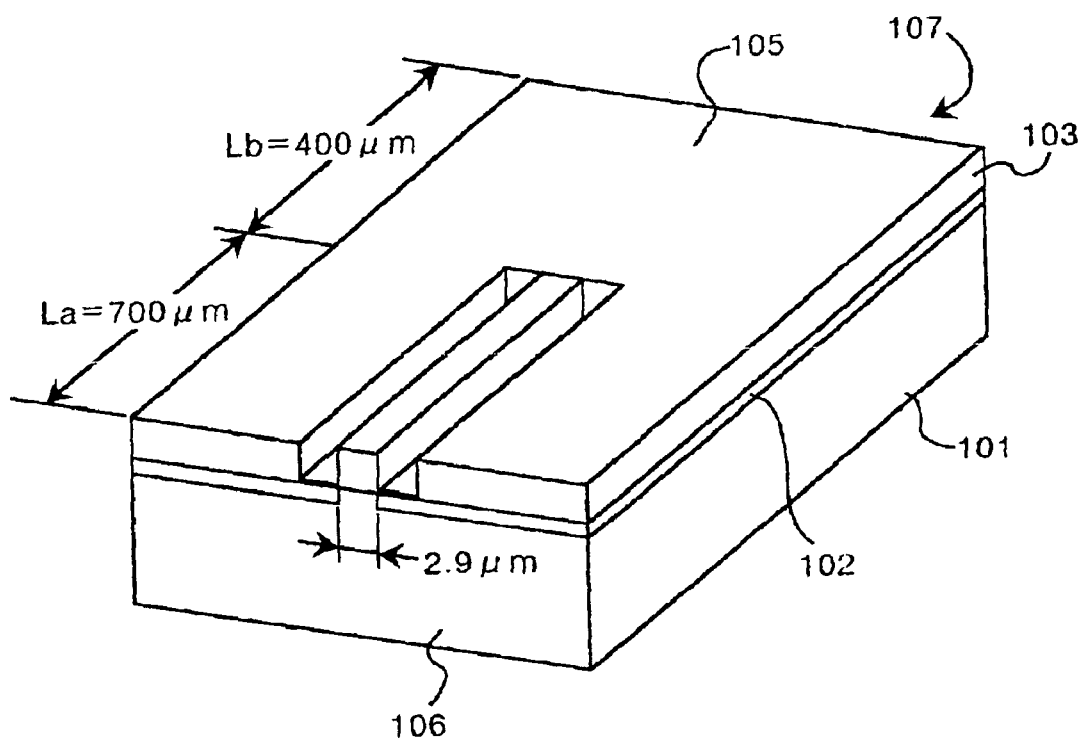
FIG. 8 is a perspective view showing the structure of the super luminescent diode.

FIG. 8 shows the detailed structure of the SLD 14. The MOVPE method is employed in forming the wafer. A quantum well active layer 102, a p-type InP cladding layer 103, and a p-type InGaAs contact layer (not shown) are formed on an n-type InP substrate 101. The grooves on both sides of the waveguide path are 10 μm wide, and are formed to a depth of approximately 0.3 μm over the active layer by wet etching. An SiO₂ film (not shown) covers the region other than the ridge portion under a p-type electrode 104. A light absorption region is provided to reduce the reflectance ratio in the rearward direction. To this end, single layer AR coatings of SiO₂ having a reflectance ratio of approximately 0.2% are also provided on both facets 106 and 107. The element has the following dimensions: the active region length La is 700 μm, the absorption region length Lb is 400 μm, and the ridge width is 2.9 μm.

As has been described above, the basic device structure of the SLD is similar to that of a semiconductor laser. However, the reflectance ratio of the facet thereof is low, in the order of less than 1%, and selectivity of the single mode is low, so light having a broad spectral width is emitted. Accordingly, it is a device that emits light having a broad spectral width like that of an LED, from a small facet like that of a semiconductor laser. By employing such a device, problems encountered by lasers that oscillate in a single mode such as fluctuations due to mode hopping or noise caused by interference are prevented. Therefore, a stable signal can be obtained with regard to measurement utilizing ATR. Further, as the facet size is small and the light emission source is a point light source, angular uncertainty is reduced when measuring angles as in ATR. Therefore, accurate ATR angular measurement becomes possible.

While the present invention has been described with reference to the preferred embodiments thereof, the invention is not to be limited to the details given herein, but may be modified within the scope of the invention hereinafter claimed.

What is claimed is:

1. A sensor utilizing attenuated total reflection, comprising:
   a dielectric block;
   a thin film layer, formed on a surface of said dielectric block, for placing a sample thereon;
   a light source for emitting a light beam;
   an optical system for making said light beam enter said dielectric block at various angles of incidence so that the condition for total internal reflection is satisfied at an interface between said dielectric block and said thin film layer; and
   photodetection means for detecting said attenuated total reflection by measuring the intensity of said light beam satisfying total internal reflection at said interface;
   wherein a semiconductor light emitting element that emits light by super radiance is employed as said light source.

2. A sensor utilizing attenuated total reflection, comprising:
   a dielectric block;
   a metal film, formed on a surface of said dielectric block, for placing a sample thereon;
   a light source for emitting a light beam;
   an optical system for making said light beam enter said dielectric block at various angles of incidence so that the condition for total internal reflection is satisfied at an interface between said dielectric block and said metal film; and
   photodetection means for detecting said attenuated total reflection that results from surface plasmon resonance by measuring the intensity of said light beam satisfying total internal reflection at said interface;
   wherein a semiconductor light emitting element that emits light by super radiance is employed as said light source.

3. A sensor utilizing attenuated total reflection, comprising:
- a dielectric block;
- a cladding layer formed on a surface of said dielectric block;
- an optical waveguide layer, formed on said cladding layer, for placing a sample thereon;
- a light source for emitting a light beam;
- an optical system for making said light beam enter said dielectric block at various angles of incidence so that the condition for total internal reflection is satisfied at an interface between said dielectric block and said cladding layer; and
- photodetection means for detecting said attenuated total reflection that results from excitation of a waveguide mode in said optical waveguide layer by measuring the intensity of said light beam satisfying total internal reflection at said interface;
- wherein a semiconductor light emitting element that emits light by super radiance is employed as said light source.

* * * * *